(12) United States Patent
Kawakami

(10) Patent No.: US 8,653,301 B2
(45) Date of Patent: Feb. 18, 2014

(54) TRICYCLODECANE MONOMETHANOL MONOCARBOXYLIC ACID AND DERIVATIVES THEREOF

(75) Inventor: Hiroyuki Kawakami, Ichihara (JP)

(73) Assignees: Hitachi Chemical Company, Ltd., Tokyo (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 13/391,656

(22) PCT Filed: Jul. 9, 2010

(86) PCT No.: PCT/JP2010/061689
§ 371 (c)(1),
(2), (4) Date: Feb. 22, 2012

(87) PCT Pub. No.: WO2011/027618
PCT Pub. Date: Mar. 10, 2011

(65) Prior Publication Data
US 2012/0157705 A1    Jun. 21, 2012

(30) Foreign Application Priority Data
Sep. 3, 2009  (JP) ................. P2009-203753

(51) Int. Cl.
*C07C 61/125*    (2006.01)
*C07C 61/135*    (2006.01)
*C07C 69/753*    (2006.01)

(52) U.S. Cl.
USPC .......................................... 562/499; 560/117

(58) Field of Classification Search
None
See application file for complete search history.

(56) References Cited

U.S. PATENT DOCUMENTS 5,194,676 A    3/1993   Castanet et al.

FOREIGN PATENT DOCUMENTS

| JP | 56-133242 | 10/1981 |
|----|-----------|---------|
| JP | 58-110538 | 7/1983 |
| JP | 0214270 | 1/1990 |
| JP | 8-311130 | 11/1996 |
| JP | 2626996 | 4/1997 |
| JP | 2002-265886 | 9/2002 |
| JP | 2006-111794 | 4/2006 |
| JP | 2006-315960 | 11/2006 |
| JP | 2007-517926 | 7/2007 |
| WO | WO 2005/061580 A1 | 7/2005 |
| WO | WO 2009/041192 | 4/2009 |

OTHER PUBLICATIONS

Database CAPLUS on STN, Acc. No. 1990:408168, KANKE, JP 02014270 A (Jan. 18, 1990) (abstract).*
Translation of the International Preliminary Report on Patentability dated Apr. 19, 2012, for International (PCT) Application No. PCT/2010/061689, filed Jul. 9, 2010.
M. Hidai, "Homogeneous Multimetallic Catalysis Part 6. Hydroformylation and Hydroesterification of Olefins by Homogeneous Cobalt-Ruthenium Bimetallic Catalysts", *Journal of Molecular Catalysis*, vol. 35, 1986, pp. 29-37.
E. M. Nahmed, et al., "Ester Formation from Ruthenium Catalyzed Alkene-Alkyl Formate Reaction", *Journal of Molecular Catalysis*, vol. 59, 1990, pp. L15-L19.
Chinese Official Action dated Sep. 23, 2013, for CN Application No. 201080037937.6.

* cited by examiner

*Primary Examiner* — Brian J Davis
(74) *Attorney, Agent, or Firm* — Antonelli, Terry, Stout & Kraus, LLP.

(57) ABSTRACT

A novel tricyclodecane monomethanol monocarboxylic acid and derivatives thereof, which can be raw materials for highly heat-resistant alicyclic polyesters, are provided. A tricyclodecane monomethanol monocarboxylic acid represented by the following formula (I) and derivatives thereof.

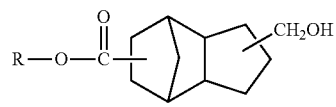

(I)

2 Claims, 1 Drawing Sheet

TRICYCLODECANE MONOMETHANOL MONOCARBOXYLIC ACID AND DERIVATIVES THEREOF

TECHNICAL FIELD

The present invention relates to a novel tricyclodecane monomethanol monocarboxylic acid and derivatives thereof, which can be raw materials for highly heat-resistant alicyclic polyesters and the like.

BACKGROUND ART

Various polyester resins are used in a wide range of fields since they can be molded into films, sheets, deformed materials, fibers, tubes, containers and the like by various molding processes and the like. Polyesters that are most frequently used are aromatic polyesters that are obtained by using an aromatic dicarboxylic acid such as terephthalic acid or isophthalic acid as a raw material, and these are excellent in heat-resistance, toughness and the like since these contain aromatic groups.

In recent years, shifting of semiconductor laser light sources to lower wavelength areas has progressed, and blue laser, UV light laser and the like have come into use as light sources for light signals. In accordance with this, demand for increase in transparency in polymer materials that are used for optical materials, electronic parts and the like has been increased. However, it was difficult to apply the above-mentioned aromatic polyesters to such fields since they are poor in ultraviolet resistance, light transmittance and the like.

Therefore, some polyesters having an alicyclic structure have been gradually used in fields for that needs the above-mentioned transparency since they are excellent in heat-resistance, transparency and water resistance. As processes for the production of alicyclic polyesters, many processes using a saturated cyclic aliphatic primary diol such as 1,4-cyclohexane dimethanol have been suggested (Patent Document 1). Since an alkylene group is inserted between a hydroxy group and a saturated cyclic aliphatic group in a saturated cyclic aliphatic primary diol, the obtained alicyclic polyester resin had aliphatic properties, and those having a cyclohexane ring backbone had low heat-resistance. Therefore, sufficient properties for the above-mentioned applications could not be obtained.

Furthermore, alicyclic polyesters composed of a dicarboxylic acid component including 4,4'-bicyclohexyldicarboxylic acid as a main component and an alicyclic diol has been suggested for improving the heat-resistance of the alicyclic polyesters (Patent Document 2). However, the heat-resistance of these was still not sufficient.

Since before, a raw material for alicyclic polyesters having excellent heat-resistance and the like has been sought.

CITATION LIST

Patent Documents

Patent Document 1: Japanese Patent Application National Publication No. 2007-517926
Patent Document 2: Japanese Patent Application Laid-Open No. 2006-111794

SUMMARY OF THE INVENTION

An embodiment of the present invention relates to a tricyclodecane monomethanol monocarboxylic acid represented by the following formula (I), and derivatives thereof.

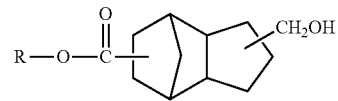

in the formula (I), R represents hydrogen, an alkyl group having 1 to 5 carbon atoms, a vinyl group or a benzyl group.

Furthermore, an embodiment of the present invention relates to a tricyclodecane monomethanol monocarboxylic acid obtained by hydroformylation of a compound represented by the following formula (II), and derivatives thereof.

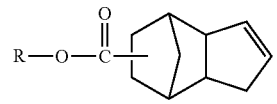

In the formula (II), R represents hydrogen, an alkyl group having 1 to 5 carbon atoms, a vinyl group or a benzyl group.

The present disclosure relates to a subject matter contained in Japanese Patent Application No. 2009-203753, filed on Sep. 3, 2009, the disclosure of which is expressly incorporated herein by reference in its entirety.

According to an embodiment of the present invention, a novel tricyclodecane monomethanol monocarboxylic acid and derivatives thereof that can be raw materials for highly heat-resistant alicyclic polyesters can be provided.

EMBODIMENTS FOR CARRYING OUT THE INVENTION

Figure 1:
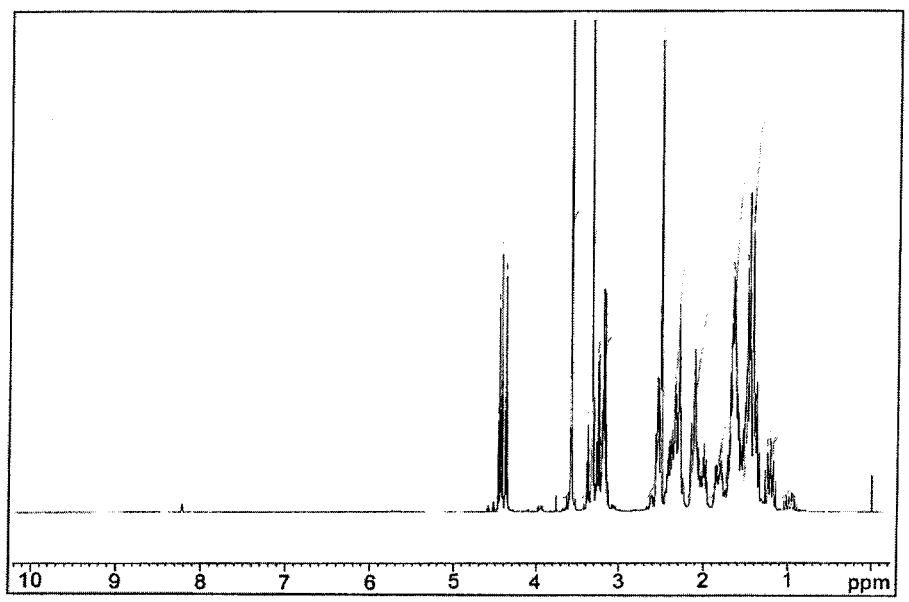
FIG. 1 is a $^1$H-NMR spectrum of methyl tricyclodecane monomethanol monocarboxylate obtained in Example 1.

Hereinafter, the present invention is explained in more detail. An embodiment of the present invention relates to a tricyclodecane monomethanol monocarboxylic acid represented by the following formula (I) and derivatives thereof.

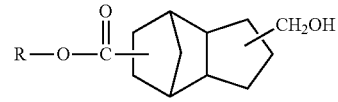

In the formula (I), R represents hydrogen; an alkyl group having 1 to 5 carbon atoms such as a methyl group, an ethyl group, a propyl group, an isopropyl group, a butyl group, a tert-butyl group and a pentyl group; a vinyl group; a benzyl group; or the like. Of these, an alkyl group having 1 to 5 carbon atoms is preferable, and a methyl group is specifically preferable from the viewpoints that they have high reactivity and that the production costs therefor are inexpensive.

In the formula (I), although the bonding positions of the two substituents, i.e., —C(O)OR and —CH$_2$OH, are not specifically limited, it is preferable that —C(O)OR binds to the 8- or 9-position of the tricyclodecane group and —CH$_2$OH binds to the 3- or 4-position of the tricyclodecane group.

Specific examples of the above-mentioned tricyclodecane monomethanol monocarboxylic acid and derivatives thereof may include 4-hydroxymethyl-8-carboxy-tricyclo[5.2.1.0$^{2,6}$]decane, 3-hydroxymethyl-8-carboxy-tricyclo[5.2.1.0$^{2,6}$]decane, 3-hydroxymethyl-9-carboxy-tricyclo[5.2.1.0$^{2,6}$]decane, 4-hydroxymethyl-8-methoxycarbonyl-tricyclo[5.2.1.0$^{2,6}$]decane, 3-hydroxymethyl-8-methoxycarbonyl-tricyclo[5.2.1.0$^{2,6}$]decane, 3-hydroxymethyl-9-methoxycarbonyl-tricyclo[5.2.1.0$^{2,6}$]decane, 4-hydroxymethyl-8-ethoxycarbonyl-tricyclo[5.2.1.0$^{2,6}$]decane, 3-hydroxymethyl-8-ethoxycarbonyl-tricyclo[5.2.1.0$^{2,6}$]decane, 3-hydroxymethyl-9-ethoxycarbonyl-tricyclo[5.2.1.0$^{2,6}$]decane, 4-hydroxymethyl-8-propoxycarbonyl-tricyclo[5.2.1.0$^{2,6}$]decane, 3-hydroxymethyl-8-propoxycarbonyl-tricyclo[5.2.1.0$^{2,6}$]decane, 3-hydroxymethyl-9-propoxycarbonyl-tricyclo[5.2.1.0$^{2,6}$]decane, 4-hydroxymethyl-8-butoxycarbonyl-tricyclo[5.2.1.0$^{2,6}$]decane, 3-hydroxymethyl-8-butoxycarbonyl-tricyclo[5.2.1.0$^{2,6}$]decane, 3-hydroxymethyl-9-butoxycarbonyl-tricyclo[5.2.1.0$^{2,6}$]decane, 4-hydroxymethyl-8-pentoxycarbonyl-tricyclo[5.2.1.0$^{2,6}$]decane, 3-hydroxymethyl-8-pentoxycarbonyl-tricyclo[5.2.1.0$^{2,6}$]decane, 3-hydroxymethyl-9-pentoxycarbonyl-tricyclo[5.2.1.0$^{2,6}$]decane, 4-hydroxymethyl-8-vinyloxycarbonyl-tricyclo[5.2.1.0$^{2,6}$]decane, 3-hydroxymethyl-8-vinyloxycarbonyl-tricyclo[5.2.1.0$^{2,6}$]decane, 3-hydroxymethyl-9-vinyloxycarbonyl-tricyclo[5.2.1.0$^{2,6}$]decane, 4-hydroxymethyl-8-benzyloxycarbonyl-tricyclo[5.2.1.0$^{2,6}$]decane, 3-hydroxymethyl-8-benzyloxycarbonyl-tricyclo[5.2.1.0$^{2,6}$]decane, 3-hydroxymethyl-9-benzyloxycarbonyl-tricyclo[5.2.1.0$^{2,6}$]decane and the like.

The tricyclodecane monomethanol monocarboxylic acid and derivatives thereof of the present invention represented by the following formula (I) can be obtained by hydroformylating a compound represented by the following formula (II) that is obtained by adding —C(O)OR to dicyclopentadiene represented by the following formula (III).

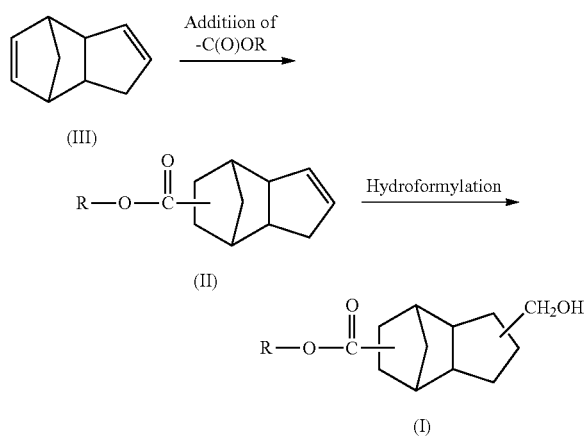

In the above-mentioned formulas (II) and (I), R represents those as mentioned above.

The compound represented by the above-mentioned formula (II) that is obtained by adding —C(O)OR to dicyclopentadiene represented by the above-mentioned formula (III) has a structure in which —C(O)OR is added to the 8- or 9-position of a tricyclo[5.2.1.0$^{2,6}$]dec-3-ene backbone.

Examples of the process for obtaining such compound represented by the above-mentioned formula (II) may include a process including reacting the dicyclopentadiene represented by the above-mentioned formula (III) with a formic acid compound (HC(O)OR), or a process including reacting the dicyclopentadiene with carbon monoxide and an alcohol (ROH). Although the process for obtaining the compound represented by the formula (II) is not specifically limited, a process including reacting the dicyclopentadiene with a formic acid compound (HCOOR) is preferable in view of the operatability, safeness and cost thereof, and the like. In the case when a formic acid wherein R is hydrogen is used as the formic acid compound, a carboxylation reaction occurs, thereby a carboxyl group can be added to the dicyclopentadiene. In the case when a formic acid ester wherein R is an alkyl group having 1 to 5 carbon atoms, a vinyl group or a benzyl group is used, a hydroesterification reaction occurs, thereby a hydroester group can be added to the dicyclopentadiene.

The hydroesterification reaction of the dicyclopentadiene is not specifically limited, and for example, a process including reacting with a formic acid ester by using a transition metal complex catalyst or the like may be exemplified, and a process including reacting the dicyclopentadiene and a formic acid ester in the presence of a catalyst system containing a ruthenium compound, a cobalt compound and a halide salt is preferable.

As the formic acid ester as the raw material for the hydroesterification reaction, a formic acid ester (HCOOR) that corresponds to the —C(O)OR of the objective tricyclodecane monomethanol monocarboxylic acid and derivatives thereof is used. Examples of such formic acid ester may include methyl formate, ethyl formate, propyl formate, isopropyl formate, butyl formate, isobutyl formate, amyl formate, isoamyl formate, vinyl formate, benzyl formate and the like. Among these, methyl formate is preferable in view of costs and reactivity.

The ruthenium compound that can be used as the catalyst for the hydroesterification reaction may be any compound including ruthenium and is not specifically limited. Specific examples of preferable compounds may include ruthenium compounds having carbonyl ligands and halogen ligands in a molecule such as [Ru(CO)$_3$Cl$_2$]$_2$, [RuCl$_2$(CO)$_2$]$_n$ (wherein n is an unspecified natural number), [Ru(CO)$_3$Cl$_3$]$^-$, [Ru$_3$(CO)$_{11}$Cl]$^-$ and [Ru$_4$(CO)$_{13}$Cl]$^-$, and the like. Of these, [Ru(CO)$_3$Cl$_2$]$_2$ and [RuCl$_2$(CO)$_2$]$_n$ are more preferable in view of improvement of a reaction rate.

The ruthenium compound having the above-mentioned ligands in combination may be prepared by using RuCl$_3$, Ru$_3$(CO)$_{12}$, RuCl$_2$(C$_8$H$_{12}$), Ru(CO)$_3$(C$_8$H$_8$), Ru(CO)$_3$(C$_8$H$_{12}$) and Ru(C$_8$H$_{10}$)(C$_8$H$_{12}$), and the like as a precursor compound. The above-mentioned ruthenium compound may also be prepared before or after the reaction of hydroesterification and introduced in the reaction system.

The use amount of the above-mentioned ruthenium compound is preferably from 1/10000 to 1 equivalent amount, more preferably from 1/1000 to 1/50 equivalent amount, with respect to 1 equivalent amount of the dicyclopentadiene as a raw material. In view of production costs, a smaller use amount of the ruthenium compound is preferable, and the reaction is quick when the amount is 1/10000 equivalent amount or more. Furthermore, 1 equivalent amount or less is economical.

The cobalt compound that can be used as the catalyst for the hydroesterification reaction may be any compound including cobalt and is not specifically limited. Specific examples of preferable compounds may include cobalt compounds having carbonyl ligands such as Co$_2$(CO)$_8$, HCo(CO)$_4$ and Co$_4$(CO)$_{12}$, cobalt compounds having carboxylic acid compounds as ligands such as cobalt acetate, cobalt propionate, cobalt benzoate and cobalt citrate, cobalt phosphate, and the like. Among these, Co$_2$(CO)$_8$, cobalt acetate and cobalt citrate are more preferable in view of improvement of a reaction rate.

The use amount of the above-mentioned cobalt compound is from 1/100 to 10 equivalent amount, preferably from 1/10 to 5 equivalent amount, with respect to 1 equivalent amount of the ruthenium compound. When the ratio of the above-mentioned cobalt compound with respect to the above-mentioned ruthenium compound is 1/100 or more and 10 or less, the production amount of the ester compound is much.

The halide salt that can be used as the catalyst for the hydroesterification reaction may be a compound that is constituted by a halogen ion such as a chloride ion, a bromide ion and an iodide ion, and a cation, and is not specifically limited. The above-mentioned cation may be either of an inorganic substance ion and an organic substance ion. Furthermore, the above-mentioned halide salt may include one or more halogen ion(s) in a molecule.

The inorganic substance ion that constitutes the halide salt may be a kind of metal ion selected from alkali metals and alkaline earth metals. Specific examples may include lithium, sodium, potassium, rubidium, cesium, calcium and strontium.

Furthermore, the organic substance ion may be an organic group of mono or more valent derived from an organic compound. Examples may include ammonium, phosphonium, pyrrolidinium, pyridium, imidazolium and iminium, and the hydrogen atoms of these ions may be substituted by hydrocarbon groups such as alkyls and aryls. Specific examples of preferable organic substance ions may include, but are not specifically limited to, tetramethylammonium, tetraethylammonium, tetrapropylammonium, tetrabutylammonium, tetrapentylammonium, tetrahexylammonium, tetraheptylammonium, tetraoctylammonium, trioctylmethylammonium, benzyltrimethylammonium, benzyltriethylammonium, benzyltributylammonium, tetramethylphosphonium, tetraethylphosphonium, tetraphenylphosphonium, benzyltriphenylphosphonium, butylmethylpyrrolidinium and bis(triphenylphosphine)iminium. Among these, quaternary ammonium salts such as butylmethylpyrrolidinium chloride, bis(triphenylphosphine)iminium iodide and trioctylmethylammonium chloride are more preferable in view of improvement of a reaction rate.

The halide salt that can be used in the present invention is not necessarily a solid salt. It may be a liquid at around room temperature or in a temperature area of 100° C. or less. It may also be an ionic liquid including a halide ion and a cation. Specific examples of the cation used for such ionic liquid may include organic substance ions such as 1-ethyl-3-methylimidazolium, 1-propyl-3-methylimidazolium, 1-butyl-3-methylimidazolium, 1-pentyl-3-methylimidazolium, 1-hexyl-3-methylimidazolium, 1-heptyl-3-methylimidazolium, 1-octyl-3-methylimidazolium, 1-decyl-3-methylimidazolium, 1-dodecyl-3-methylimidazolium, 1-tetradecyl-3-methylimidazolium, 1-hexadecyl-3-methylimidazolium, 1-octadecyl-3-methylimidazolium, 1-ethyl-2,3-dimethylimidazolium, 1-butyl-2,3-dimethylimidazolium, 1-hexyl-2,3-dimethylimidazolium, 1-ethylpyridinium, 1-butylpyridinium, 1-hexylpyridinium, 8-methyl-1,8-diazabicyclo[5.4.0]-7-undecene, 8-ethyl-1,8-diazabicyclo[5.4.0]-7-undecene, 8-propyl-1,8-diazabicyclo[5.4.0]-7-undecene, 8-butyl-1,8-diazabicyclo[5.4.0]-7-undecene, 8-pentyl-1,8-diazabicyclo[5.4.0]-7-undecene, 8-hexyl-1,8-diazabicyclo[5.4.0]-7-undecene, 8-heptyl-1,8-diazabicyclo[5.4.0]-7-undecene and 8-octyl-1,8-diazabicyclo[5.4.0]-7-undecene. In the present invention, the above-mentioned halide salts may be used solely, or as a combination of plural numbers.

Among the above-mentioned halide salts, preferable halide salts are chloride salts, bromide salts and iodide salts, wherein the cation is an organic substance ion. Specific examples of preferable halide salts in the present invention may include, but are not limited to, butylmethylpyrrolidinium chloride, bis(triphenylphosphine)iminium iodide, trioctylmethylammonium chloride and the like.

The addition amount of the halide salt is, for example, from 1 to 1,000 equivalent amounts, preferably from 2 to 50 equivalent amounts, with respect to 1 equivalent amount of the ruthenium compound. By adjusting the addition amount to 1 equivalent amount or more, the reaction velocity can be increased effectively. On the other hand, when the addition amount is 1,000 equivalent amount or less, the effect of promoting the reaction is significant.

In the hydroesterification by the reaction of the above-mentioned dicyclopentadiene and formic acid ester, the effect of promoting the reaction by the specific catalyst system containing the ruthenium compound, the cobalt compound and the halide salt can further be increased by optionally adding a basic compound, a phenol compound or an organic halogen compound to the above-mentioned catalyst system.

The above-mentioned basic compound may be an inorganic compound or an organic compound. Specific examples of the basic inorganic compound may include carbonates, hydrogen carbonates, hydroxide salts, alkoxides and the like of alkali metals and alkaline earth metals. Specific examples of the basic organic compound may include primary amine compounds, secondary amine compounds, tertiary amine compounds, pyridine compounds, imidazole compounds and quinoline compounds. Among the above-mentioned basic compounds, tertiary amine compounds are preferable in view of the effect of promoting the reaction. Specific examples of preferable tertiary amines that can be used in the present invention may include trialkylamine, N-alkylpyrrolidine, quinuclidine and triethylenediamine, and the like.

Although the addition amount of the basic compound is not specifically limited, it is from 1 to 1,000 equivalent amount, preferably from 2 to 200 equivalent amount, with respect to 1 equivalent amount of the ruthenium compound. By adjusting the addition amount to 1 equivalent amount or more, exhibition of the effect of promoting the reaction tends to be more significant. Furthermore, when the addition amount is 1,000 equivalent amount or less, the effect of promoting the reaction is significant.

The above-mentioned phenol compound is not specifically limited. Specific examples of the phenol compound that can be used may include phenol, cresol, alkylphenols, methoxyphenol, phenoxyphenol, chlorophenol, trifluoromethylphenol, hydroquinone and catechol, and the like.

Although the addition amount of the phenol compound is not specifically limited, it is from 1 to 1,000 equivalent amount, preferably from 2 to 200 equivalent amount, with respect to 1 equivalent amount of the ruthenium compound. By adjusting the addition amount to 1 equivalent amount or more, exhibition of the effect of promoting the reaction tends to be more significant. Furthermore, when the addition amount is 1,000 equivalent amount or less, it is economical and the effect of promoting the reaction is significant.

Although the above-mentioned organic halogen compound is not specifically limited, specific examples of the organic halogen compound that can be used may include monohalogenated methanes, dihalogenated methanes, dihalogenated ethanes, trihalogenated methanes, tetrahalogenated methanes, halogenated benzenes and the like.

The addition amount of the organic halogen compound is, but is not specifically limited to, for example, from 1 to 1,000 equivalent amount, preferably from 2 to 200 equivalent amount, with respect to 1 equivalent amount of the ruthenium compound. By adjusting the addition amount to 1 equivalent amount or more, exhibition of the effect of promoting the reaction tends to be more significant. Furthermore, when the addition amount is 1,000 equivalent amount or less, the effect of promoting the reaction is significant.

The hydroesterification by the reaction of the above-mentioned dicyclopentadiene and formic acid ester can be proceeded without using a specific solvent. However, where necessary, a solvent may be used. The solvent that can be used is not specifically limited as long as it can dissolve the compounds that are used as raw materials. Specific examples of the solvent that can preferably be used may include n-pentane, n-hexane, n-heptane, cyclohexane, benzene, toluene, o-xylene, p-xylene, m-xylene, ethylbenzene, cumene, tetrahydrofuran, N-methylpyrrolidone, dimethylformamide, dimethylacetamide, dimethylimidazolidinone, ethyleneglycol dimethyl ether, diethyleneglycol dimethyl ether, triethyleneglycol dimethyl ether and the like.

The hydroesterification by the reaction of the above-mentioned dicyclopentadiene and formic acid ester is carried out preferably at a temperature range of from 80° C. to 200° C., more preferably at a temperature range of from 100° C. to 160° C. By carrying out the reaction at a temperature of 80° C. or more, the reaction velocity is quicken, thereby the reaction is proceeded easily with a high efficiency. On the other hand, by controlling the reaction temperature to 200° C. or less, the decomposition of the formic acid ester that is used as a raw material can be suppressed. When the formic acid ester is decomposed, addition of ester groups to the dicyclopentadiene is not achieved, and thus a too high reaction temperature is not desirable. In the case when the reaction temperature exceeds the boiling point of the dicyclopentadiene or formic acid ester used as a raw material, the reaction must be conducted in a pressure-resistant container. The termination of the reaction can be confirmed by using a well-known analysis technique such as gaschromatograph and NMR. Furthermore, it is preferable that the reaction is carried out under an inert gas atmosphere such as nitrogen and argon.

The tricyclodecane monomethanol monocarboxylic acid and derivatives thereof of the present invention represented by the above-mentioned formula (I) can be obtained by hydroformylating a compound represented by the following formula (II) that is obtained by adding —C(O)OR to the above-mentioned dicyclopentadiene.

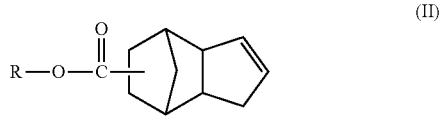

(II)

In the formula (II), R represents the same as mentioned above.

The tricyclodecane monomethanol monocarboxylic acid and derivatives thereof of the present invention that are obtained by hydroformylation of the compound represented by the above-mentioned formula (II) each have a structure in which —$CH_2OH$ is added to the 3- or 4-position of a tricyclo [$5.2.1.0^{2,6}$]decane backbone.

The hydroformylation of the compound represented by the formula (II) is not specifically limited, and for example, the process described in Shokubai Kouza (Catalyst Courses) Vol. 7, Catalyst Society of Japan ed., Kodansha (1985), which includes reacting carbon monoxide and hydrogen by using a transition metal complex catalyst such as cobalt, ruthenium and rhodium and adding an aldehyde, followed by further hydrogenation; the process described in Japanese Patent No. 3343585 or Japanese Patent No. 3702343, and the like, which includes hydroformylation by using carbon dioxide, hydrogen and a ruthenium compound catalyst; the process described in International Publication No. 2009/041192, which includes hydroformylation by using carbon dioxide, hydrogen and a catalyst system including a ruthenium compound and a cobalt compound in combination; and the like can be used. From the viewpoints of operatability, safeness, reactivity and the like, the process including hydroformylation using carbon dioxide, hydrogen and a catalyst system including a ruthenium compound and a cobalt compound in combination is preferable. The entirety of the above-mentioned documents are incorporated herein by reference.

For the process including hydroformylation using carbon dioxide and hydrogen, which can be used in the present invention, a raw material gas containing carbon dioxide and hydrogen as main components can be used as a raw material. Although the content of the carbon dioxide in the raw material gas is not specifically limited, it is preferably from 10 to 95 vol %, more preferably from 50 to 80 vol %. Furthermore, although the content of the hydrogen in the raw material gas is not specifically limited, it is preferably from 5 to 90 vol %, more preferably from 20 to 50 vol %. These may be fed in the form of a mixed gas, or may be fed separately. When the content of the hydrogen is 90 vol % or less, hydrogenation of the raw materials is hard to be occur, and when the content is 5 vol % or more, the reaction velocity is high. It is not completely necessary that carbon monoxide is incorporated in the raw material gas, but no problem is caused even if carbon monoxide is incorporated.

The ruthenium compound that can be used as a catalyst for the hydroformylation reaction is not specifically limited as long as it includes ruthenium. Specific examples of the preferable compounds may include ruthenium compounds having carbonyl ligands and halogen ligands in a molecule such as $[Ru(CO)_3Cl_2]_2$, $[RuCl_2(CO)_2]_n$ (wherein n is an unspecified natural number), $[Ru(CO)_3Cl_3]^-$, $[Ru_3(CO)_{11}Cl]^-$ and $[Ru_4(CO)_{13}Cl]^-$, and the like, of which $[Ru(CO)_3Cl_2]_2$ and $[RuCl_2(CO)_2]_n$ are preferable in view of improvement of a reaction rate.

The ruthenium compound having the above-mentioned ligands in combination may be prepared by using $RuCl_3$, $Ru_3(CO)_{12}$, $RuCl_2(C_8H_{12})$, $Ru(CO)_3(C_8H_8)$, $Ru(CO)_3(C_8H_{12})$ and $Ru(C_8H_{10})(C_8H_{12})$, and the like as a precursor compound. The above-mentioned ruthenium compound may also be prepared before or after the reaction of hydroformylation and introduced in the reaction system.

The use amount of the above-mentioned ruthenium compound is preferably from 1/10000 to 1 equivalent amount, more preferably from 1/1000 to 1/50 equivalent amount, with respect to 1 equivalent amount of the compound represented by the formula (II) as a raw material. In view of production costs, a smaller use amount of the ruthenium compound is preferable. The reaction is quick when the amount is 1/10000 equivalent amount or more. Furthermore, 1 equivalent amount or less is economical.

The cobalt compound that can be used as the catalyst for the hydroformylation reaction is not specifically limited as long as it includes cobalt. Specific examples of preferable compounds may include cobalt compounds having carbonyl ligands such as $Co_2(CO)_8$, $HCo(CO)_4$ and $Co_4(CO)_{12}$, cobalt compounds having carboxylic acid compounds as ligands such as cobalt acetate, cobalt propionate, cobalt benzoate and cobalt citrate, cobalt phosphate, and the like. Among these, $Co_2(CO)_8$, cobalt acetate and cobalt citrate are more preferable in view of improvement of a reaction rate.

The use amount of the above-mentioned cobalt compound is from 1/100 to 10 equivalent amount, preferably from 1/10 to 5 equivalent amount, with respect to 1 equivalent amount of the ruthenium compound. When the ratio of the above-mentioned cobalt compound with respect to the above-mentioned ruthenium compound is 1/100 or more and 10 or less, the production amount of the tricyclodecane monomethanol monocarboxylic acid and derivatives thereof is much.

In the hydroformylation of the compound represented by the formula (II) that can be used in the present invention, the effect of promoting the reaction by the above-mentioned catalyst system can further be increased by optionally adding a halide salt or an acid to the specific catalyst system including a ruthenium compound and a cobalt compound.

The halide salt that can be used in the present invention is not specifically limited as long as it is a compound that is constituted by a halogen ion such as a chloride ion, a bromide ion and an iodide ion, and a cation. The above-mentioned cation may be either of an inorganic substance ion and an organic substance ion. Furthermore, the above-mentioned halide salt may include one or more halogen ion(s) in a molecule.

The inorganic substance ion that constitutes the halide salt may be a kind of metal ion selected from alkali metals and alkaline earth metals. Specific examples may include lithium, sodium, potassium, rubidium, cesium, calcium and strontium.

Furthermore, the organic substance ion may be an organic group of mono- or more valent derived from an organic compound. Examples may include ammonium, phosphonium, pyrrolidinium, pyridium, imidazolium and iminium, and the hydrogen atoms of these ions may be substituted by hydrocarbon groups such as alkyls and aryls. Specific examples of preferable organic substance ions may include, but are not specifically limited to, tetramethylammonium, tetraethylammonium, tetrapropylammonium, tetrabutylammonium, tetrapentylammonium, tetrahexylammonium, tetraheptylammonium, tetraoctylammonium, trioctylmethylammonium, benzyltrimethylammonium, benzyltriethylammonium, benzyltributylammonium, hexadecyltrimethylammonium, tetramethylphosphonium, tetraethylphosphonium, tetraphenylphosphonium, benzyltriphenylphosphonium, butylmethylpyrrolidinium and bis(triphenylphosphine)iminium. Among these, quaternary ammonium salts such as hexadecyltrimethylammonium chloride and hexadecyltrimethylammonium bromide are more preferable in view of improvement of a reaction rate.

The halide salt that can be used in the present invention is not necessarily a solid salt. It may be a liquid at around room temperature or in a temperature area of 100° C. or less. It may also be an ionic liquid including a halide ion and a cation. Specific examples of the cation used for such ionic liquid may include organic substance ions such as 1-ethyl-3-methylimidazolium, 1-propyl-3-methylimidazolium, 1-butyl-3-methylimidazolium, 1-pentyl-3-methylimidazolium, 1-hexyl-3-methylimidazolium, 1-heptyl-3-methylimidazolium, 1-octyl-3-methylimidazolium, 1-decyl-3-methylimidazolium, 1-dodecyl-3-methylimidazolium, 1-tetradecyl-3-methylimidazolium, 1-hexadecyl-3-methylimidazolium, 1-octadecyl-3-methylimidazolium, 1-ethyl-2,3-dimethylimidazolium, 1-butyl-2,3-dimethylimidazolium, 1-hexyl-2,3-dimethylimidazolium, 1-ethylpyridinium, 1-butylpyridinium, 1-hexylpyridinium, 8-methyl-1,8-diazabicyclo[5.4.0]-7-undecene, 8-ethyl-1,8-diazabicyclo[5.4.0]-7-undecene, 8-propyl-1,8-diazabicyclo[5.4.0]-7-undecene, 8-butyl-1,8-diazabicyclo[5.4.0]-7-undecene, 8-pentyl-1,8-diazabicyclo[5.4.0]-7-undecene, 8-hexyl-1,8-diazabicyclo[5.4.0]-7-undecene, 8-heptyl-1,8-diazabicyclo[5.4.0]-7-undecene and 8-octyl-1,8-diazabicyclo[5.4.0]-7-undecene. In the present invention, the above-mentioned halide salts may be used solely, or as a combination of plural numbers.

Among the above-mentioned halide salts, preferable halide salts are chloride salts, bromide salts and iodide salts, wherein the cation is an organic substance ion. Specific examples of preferable halide salts in the present invention may include, but are not limited to, hexadecyltrimethylammonium chloride, hexadecyltrimethylammonium bromide and the like.

The addition amount of the halide salt is, for example, from 1 to 1,000 equivalent amounts, preferably from 2 to 50 equivalent amounts, with respect to 1 equivalent amount of the ruthenium compound. By adjusting the addition amount to 1 equivalent amount or more, the reaction velocity can be increased effectively. On the other hand, when the addition amount is 1,000 equivalent amount or less, the effect of promoting the reaction is significant.

As the acid that can be used in the present invention, all acids that are applicable to the Lewis's definition can be used. According to this definition, when a certain substance A is fed an electron pair from another substance B, A is defined as an acid and B is defined as a base, and all substances that are applicable to A that accepts an electron pair can be used.

The above-mentioned acid is preferably an acid in which A is a proton donor, i.e., a Bronsted acid. As the Bronsted acid, for example, hydrochloric acid, sulfuric acid, nitric acid, phosphoric acid, methylphosphoric acid, alkylphosphoric acids, phenylphosphoric acid, diphenyl phosphite, phenylphosphonic acid, phenylphosphinic acid, boric acid, phenylboric acid, trifluoromethanesulfonic acid, paratoluenesulfonic acid, phenol, tungstic acid, phosphotungstic acid; and alkylcarboxylic acids such as formic acid, acetic acid, trifluoroacetic acid, propionic acid and butyric acid; aromatic carboxylic acids such as benzoic acid, phthalic acid and salicylic acid, and the like are used, and acids including phosphorus such as phosphoric acid, alkylphosphoric acids and phenylphosphoric acid are preferable.

The addition amount of the acid, is, for example, from 0.1 to 100 equivalent amount, preferably from 1 to 10 equivalent amount, with respect to 1 equivalent amount of the ruthenium compound. By adjusting the addition amount to 0.1 equivalent amount or more, the reaction velocity can be increased effectively. On the other hand, when the addition amount is 100 equivalent amount or less, the effect of promoting the reaction is significant.

The hydroformylation reaction in the present invention can use a solvent, if necessary. The solvent that can be used is not specifically limited as long as it can dissolve the compound represented by the above-mentioned formula (II). Specific examples of the solvent that can be used preferably may include n-pentane, n-hexane, n-heptane, cyclohexane, benzene, toluene, o-xylene, p-xylene, m-xylene, ethylbenzene, cumene, tetrahydrofuran, N-methylpyrrolidone, dimethylformamide, dimethylacetamide, dimethylimidazolidinone, ethyleneglycol dimethyl ether, diethyleneglycol dimethyl ether, triethyleneglycol dimethyl ether and the like. When the solvent is used, the preferable use amount thereof is within the range that the concentration of the compound represented by the above-mentioned formula (II) is from 10 to 1000% by weight.

The hydroformylation is preferably carried out at a temperature range of from 100° C. to 200° C., more preferably carried out at a temperature range of from 100° C. to 180° C., specifically preferably carried out at a temperature range of from 120° C. to 160° C. By carrying out the reaction at a temperature of 100° C. or more, the reaction velocity is quicken, and the reaction becomes easy to be proceeded with a fine efficiency. Meanwhile, by adjusting the reaction temperature to 200° C. or less, hydrogenation of the unsaturated bonds in the compound represented by the above-mentioned formula (II) can be suppressed. Since hydroformylation is not achieved when hydrogenation of the unsaturated bonds in the compound represented by the formula (II) occurs, a too high reaction temperature is not desirable.

It is necessary that the hydroformylation is carried out in a pressure-resistant container. The pressure for the reaction is preferably carried out at a range of from 1 MPa to 50 MPa, more preferably carried out at a range of from 2 MPa to 15 MPa. When the pressure is 1 MPa or more, the reaction is quick, and when the pressure is 50 MPa or less, the effect of promoting the reaction is significant.

The tricyclodecane monomethanol monocarboxylic acid and derivatives thereof of the present invention are useful as raw materials for alicyclic polyesters, and polyesters using them are excellent in heat-resistance and transparency, and thus can be used as electronic parts that are used for semiconductors and liquid crystals, optical materials including optical fibers, optical lenses and the like, and as display-related materials and medical materials.

EXAMPLES

Hereinafter, the present invention is explained in more detail by Examples. However, the scope of the present invention should not be construed to be limited by the following Examples.

Example 1

Synthesis of Methyl Tricyclodecane Monocarboxylate

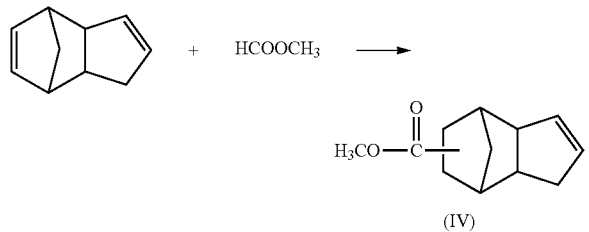

Under room temperature, in a pressurization reaction apparatus made of stainless having an inner volume of 50 ml, 10.0 mmol of dicyclopentadiene and 5.0 ml of methyl formate were added to a catalyst system that was obtained by mixing 0.025 mmol of $[Ru(CO)_3Cl_2]_2$ as a ruthenium compound, 0.025 mmol of $Co_2(CO)_8$ as a cobalt compound, 0.5 mmol of butylmethylpyrrolidinium chloride as a halide salt, 2.0 mmol of N-methylpyrrolidine as a basic compound, and 0.5 mmol of p-cresol as a phenol compound. The reaction apparatus was then purged with nitrogen gas at 0.5 MPa and retained at 120° C. for 8 hours. The inside of the reaction apparatus was then cooled to room temperature, the pressure was discharged, and a part of the residual organic phase was removed and analyzed by using gaschromatograph. According to the result of the analysis, 9.05 mmol (yield 90.5% on the basis of dicyclopentadiene) of methyl tricyclodecane monocarboxylate represented by the above-mentioned formula (IV) was generated. As a result of an analysis using a gas chromatograph-mass spectrometer (GC-MS), it was found that the obtained methyl tricyclodecane monocarboxylate was a mixture of 8-methoxycarbonyl-tricyclo[5.2.1.0$^{2,6}$]dec-3-ene and 9-methoxycarbonyl-tricyclo[5.2.1.0$^{2,6}$]dec-3-ene. The obtained methyl tricyclodecane monocarboxylate was isolated by distillation under a reduced pressure.

Synthesis of Methyl Tricyclodecane Monomethanol Monocarboxylate

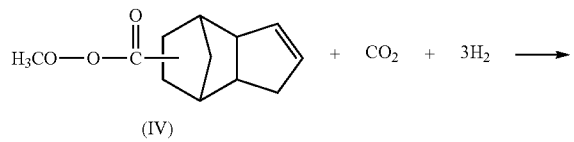

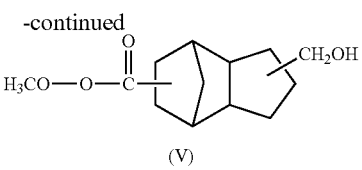

Under room temperature, in a pressurization reaction apparatus made of stainless having an inner volume of 50 ml, 10.0 mol of the methyl tricyclodecane monocarboxylate that was isolated as mentioned above and 10.0 mL of toluene as a solvent were added to a catalyst system that was obtained by mixing 0.05 mmol of $Ru_2(CO)_6Cl_4$ as a ruthenium compound, 0.05 mol of $Co_2(CO)_8$ as a cobalt compound, 2.5 mmol of hexadecyltrimethylammonium chloride as a halide salt and 0.25 mol of diphenyl phosphite as an acid and dissolved by stirring, 4 MPa of carbon dioxide and 4 MPa of hydrogen were injected, and the reaction apparatus was retained at 140° C. for 15 hours. The inside of the reaction apparatus was then cooled to room temperature, the pressure was discharged, and a part of the residual organic phase was removed and analyzed by using gaschromatograph. According to the result of the analysis, the conversion of methyl tricyclodecane monocarboxylate was 100%, and 7.45 mmol (yield 74.5% on the basis of methyl tricyclodecane monocarboxylate) of methyl tricyclodecane monomethanol monocarboxylate represented by the above-mentioned formula (V) was generated. As a result of an analysis using a gas chromatograph-mass spectrometer (GC-MS), it was found that the obtained methyl tricyclodecane monomethanol monocarboxylate was a mixture of 4-hydroxymethyl-8-methoxycarbonyl-tricyclo[5.2.1.0$^{2,6}$]decane, 3-hydroxymethyl-8-methoxycarbonyl-tricyclo[5.2.1.0$^{2,6}$]decane and 3-hydroxymethyl-9-methoxycarbonyl-tricyclo[5.2.1.0$^{2,6}$]decane.

The methyl tricyclodecane monomethanol monocarboxylate obtained as above was isolated by distillation under a reduced pressure, and a $^1$H-NMR spectrum and an IR spectrum were measured.

Meanwhile, the $^1$H-NMR spectrum was measured by putting the sample into dimethylsulfoxide (DMSO-d6) to give a solution, putting the solution into a sample tube having a diameter of 5 mm, and using a 400 MHz nuclear magnetic resonance apparatus "AV400M" manufactured by BRUKER. Furthermore, the IR spectrum was measured by using a Fourier conversion infrared spectrometer (JIR-6500, manufactured by JEOL Ltd.).

The $^1$H-NMR spectrum is shown in FIG. 1. The respective protons were attributed as shown below. For the sake of convenience of analysis, 4-hydroxymethyl-8-carboxy-tricyclo[5.2.1.0$^{2,6}$]decane represented by the following formula is shown as an example.

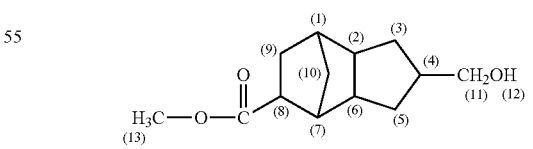

Proton (1): a peak at approximately 2.1 ppm
Proton (2): a peak at approximately 2.4 ppm
Proton (3): peaks at approximately 1.2 ppm and approximately 1.7 ppm
Proton (4): a peak at approximately 2.3 ppm
Proton (5): peaks at approximately 1.2 ppm and approximately 1.8 ppm Proton (6): a peak at approximately 2.6 ppm
Proton (7): a peak at approximately 2.1 ppm
Proton (8): a peak at approximately 1.9 ppm
Proton (9): peaks at approximately 0.9 ppm and approximately 1.7 ppm
Proton (10): a peak at approximately from 1.4 to 1.5 ppm
Proton (11): a peak at approximately 3.2 ppm
Proton (12): a peak at approximately 4.4 ppm
Proton (13): a peak at approximately 3.6 ppm Furthermore, the integral intensity ratio of the protons (1) to (10) of the tricyclodecane moiety/the proton (11) of the hydroxymethyl group/the proton (12) of the hydroxymethyl group/the proton (13) of the methoxycarbonyl group was 13.93/2.00/1.04/3.08 (theoretical value: 14/2/1/3), and thus it could be confirmed that the obtained methyl tricyclodecane monomethanol monocarboxylate had the structure represented by the following formula (I).

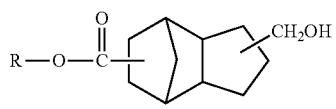

(I)

Figure 2:
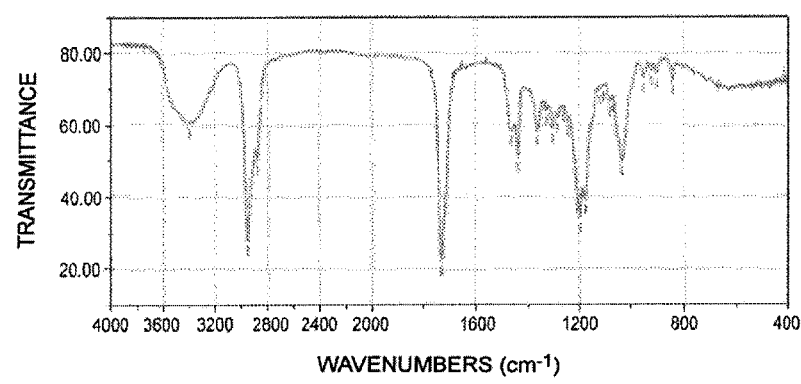
FIG. 2 is an FT-IR spectrum of methyl tricyclodecane monomethanol monocarboxylate obtained in Example 1.

Furthermore, the IR spectrum is shown in FIG. 2. The peaks of the methylene group and methine group in the tricyclodecane moiety could be confirmed at approximately from 800 to 1450 cm$^{-1}$, the peak of the methylene group attributed to the hydroxymethyl group could be confirmed at approximately 1465 cm$^{-1}$, the peak of the hydroxy group attributed to the hydroxymethyl group could be confirmed at approximately 3400 cm$^{-1}$ in broad, the peak of the carbonyl group attributed to the methoxycarbonyl group could be confirmed at approximately 1760 cm$^{-1}$, and the peaks of the methyl group attributed to the methoxycarbonyl group could be confirmed at approximately 2870 cm$^{-1}$ and 2960 cm$^{-1}$.

Reference Example

Synthesis of Polyester Having Tricyclodecane Backbone 5 g of the methyl tricyclodecane monomethanol monocarboxylate obtained in Example 1 and 0.5 g of titanium tetraisopropoxide were charged in a 10 ml flask equipped with a stirrer, a nitrogen introduction tube and a cooling tube, and stirred in an oil bath at 130° C. for 6 hours to give a polyester having a tricyclodecane backbone having a number average molecular weight of 30,000.

The glass transition temperature (Tg) and thermal decomposition initiation temperature (5% weight decrease temperature, Td$_5$) of the obtained polyester having a tricyclodecane backbone were measured under the following conditions.

The results are shown in Table 1.

(1) Glass Transition Temperature (Tg)

Measured by using a differential scanning calorimeter (Type 8230 DSC, manufactured by Rigaku Corporation).
Temperature rise velocity: 5° C./min
Atmosphere: air (2) Thermal Decomposition Initiation Temperature (5% Weight Decrease Temperature, Td$_5$)

Measured by using a differential thermal balance (Type 5200 TG-DTA, manufactured by Seiko Instruments Inc.).
Temperature rise velocity: 5° C./min
Atmosphere: air Furthermore, the light transmittances at the respective wavelengths of the obtained polyester having a tricyclodecane backbone were measured by using a Type 570 UV/VIS spectrophotometer manufactured by JASCO Corporation. The evaluation results are collectively shown in Table 1.

TABLE 1

| Item | | | Reference Example |
|---|---|---|---|
| Characteristics of polymer | Glass transition temperature (° C.) | | 160 |
| | Thermal decomposition initiation temperature (° C.) | | 417 |
| | Light transmittance (%) | 400 nm | 100 |
| | | 500 nm | 100 |
| | | 600 nm | 100 |

As shown in Table 1, the glass transition temperature of the polyester using the derivative of the tricyclodecane monomethanol monocarboxylic acid of the present invention is high as 160° C., and the thermal decomposition initiation temperature is very high as 417° C. Therefore, it was found that the obtained polyester had very excellent heat-resistance. Furthermore, it was found that the polyester had sufficient light transmittance since the light transmittance of the polyester was 100% at all wavelengths.

The invention claimed is:

1. A tricyclodecane monomethanol monocarboxylic acid represented by the following formula (I),

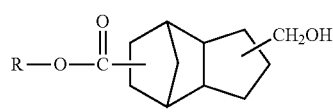

(I)

wherein R is selected from the group consisting of hydrogen, an alkyl group having 1 to 5 carbon atoms, a vinyl group, and a benzyl group.

2. A tricyclodecane monomethanol monocarboxylic acid obtained by hydroformylation of a compound represented by the following formula (II),

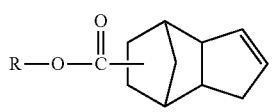

(II)

wherein R is selected from the group consisting of hydrogen, an alkyl group having 1 to 5 carbon atoms, a vinyl group, and a benzyl group.

* * * * *